United States Patent [19]

Hickel et al.

[11] Patent Number: 5,141,311
[45] Date of Patent: Aug. 25, 1992

[54] EXAMINATION OF THE PHYSICAL PROPERTIES OF THIN FILMS

[75] Inventors: Werner Hickel, Mannheim; Wolfgang Knoll, Mainz, both of Fed. Rep. of Germany

[73] Assignee: BASF Aktiengesellschaft, Ludwigshafen, Fed. Rep. of Germany

[21] Appl. No.: 517,739

[22] Filed: May 2, 1990

[30] Foreign Application Priority Data

May 3, 1989 [DE] Fed. Rep. of Germany ....... 3914631

[51] Int. Cl.⁵ .............................................. G01N 21/41
[52] U.S. Cl. .................................... 356/136; 356/369; 385/27; 385/29; 385/31
[58] Field of Search ............... 356/128, 136, 369, 382; 350/96.19; 385/27, 29, 31, 36, 39

[56] References Cited

U.S. PATENT DOCUMENTS 4,332,476 6/1982 Stenberg et al. .
4,844,613 7/1989 Batchelder et al. ................ 356/445

OTHER PUBLICATIONS

Wei et al., "A new method for determining thin film refractive index and thickness using guided optical waves", Appl. Phys. Lett. 32(12) Jun. 15, 1978.
Surface Plasmon Microscopy, Rothenhaüsler et al. Nature vol. 332, Apr. 14, 1988.
Integrated Optics and New Wave Phenomena . . . , Tien, Rev. Mod. Phys. vol. 49, No. 2, Apr. 2, 1977.
Modes of Propagating Light Waves in Thin Deposited Semiconductor Films, Applied Physics Letters, vol. 14, No. 9, May 1, 1969.
Thin Grating Couplers for Integrated Optics: . . . , Dalgoutte et al., Applied Optics, vol. 14, No. 12, Dec. 1975.
Handbuch Der Physik, Wolter, S. Flügge, Springer-Verlag, Band XXIV, 1956, pp. 461–554.

Primary Examiner—Richard A. Rosenberger
Attorney, Agent, or Firm—Keil & Weinkauf

[57] ABSTRACT

The physical properties of thin films can be examined with the aid of polarized light with which the film to be examined is irradiated while the reflected or transmitted light is deflected in the direction of an imaging system, the polarized light having the effect of exciting waveguide modes in the film to be examined.

5 Claims, 2 Drawing Sheets

EXAMINATION OF THE PHYSICAL PROPERTIES OF THIN FILMS The present invention relates to a method for examining the physical properties of thin films with the aid of polarized light.

Figure 1:
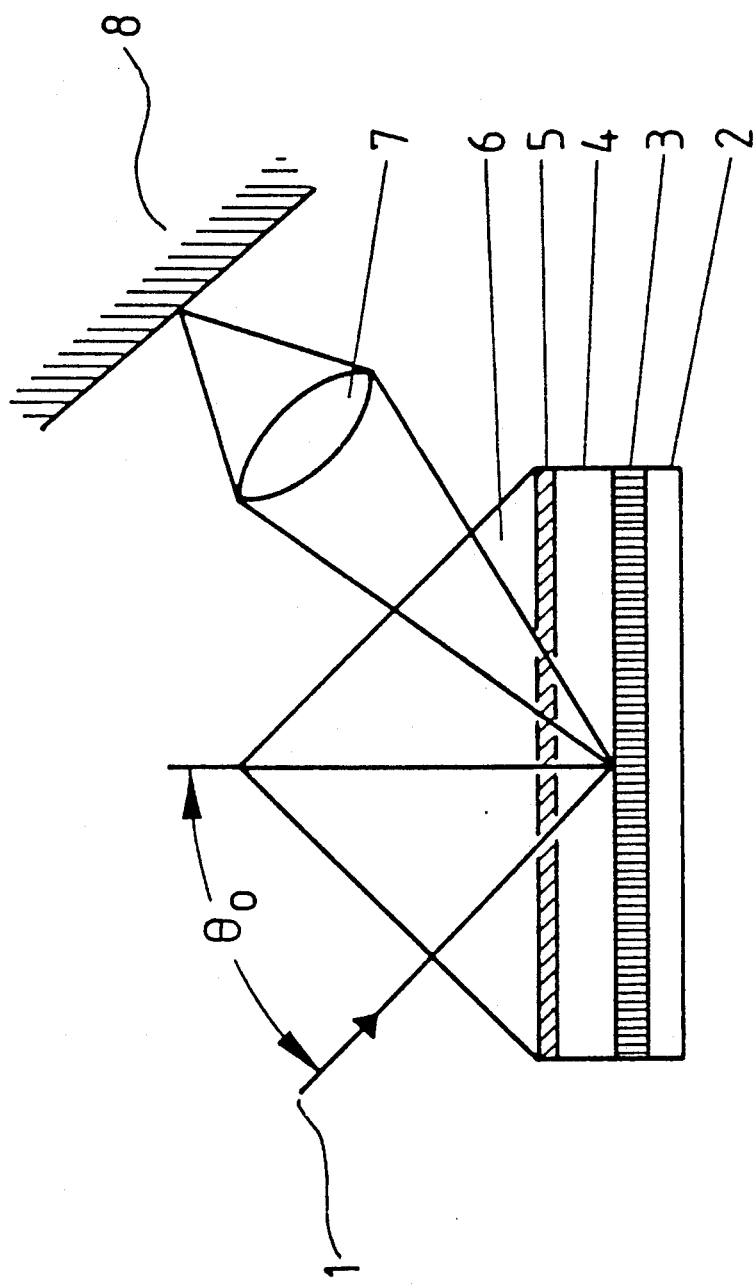
FIG. 1 shows schematically the construction of an apparatus used for the technique in accordance with this invention.

Optical imaging techniques for examining and characterizing the physical properties of surfaces in gaseous and liquid environments are of interest in many areas of science and technology. Especially methods for examining thin and ultrathin dielectric coatings ranging in thickness from a few $\mu m$ to the subnanometer range are increasingly required in physics, chemistry, microlithography, sensor systems and immunology. The methods all share the common aim of depicting surface structures with maximum lateral resolution and contrast.

Possible methods for examining thin and ultrathin films with high contrast are imaging null ellipsometry (cf. EP-A-19 088) and surface plasmon microscopy (cf. B. Rothenhäusler, W. Knoll, Nature, 332 (1988), 615). The disadvantage of imaging null ellipsometry is the complexity of the equipment and the restriction to monochromatic light. By contrast, a surface plasmon microscope has only a few optical components. In addition, this technique gives a higher contrast, especially in the subnanometer range (cf. B. Rothenhäusler, Thesis Munich (1987)). However, surface plasmon microscopy is limited to films less than 100 nm in thickness.

It is an object of the present invention to provide a method which with a minimum of technical complexity makes it possible to examine not only thin but even ultrathin films in respect of surface and refractive index structures with high intensity contrast, i.e. high vertical resolution, and good lateral resolution.

We have found that this object is achieved by the present invention by a method for examining the physical properties of thin films with the aid of polarized light with which the layer or layer system to be examined is irradiated while the reflected or transmitted light is deflected in the direction of an imaging system, wherein the polarized light has the effect of exciting waveguide modes in the layer or layer system to be examined.

This layer or layer system to be examined can be situated on any desired solid surface, for example a metal or semiconductor film.

Waveguide modes are preferably excited in the layer or layer systems to be examined using a coupling arrangement.

The coupling arrangement used is preferably a prism whose base is either situated at a distance of from 100 to 400 nm upon the layer or layer system to be examined or coated directly with the layer or layer system to be examined on top of a metal or semiconductor film.

However, the coupling arrangement used can advantageously also be a grid structure on a solid surface supporting the layer or layer system to be examined.

Surprisingly, the method according to the present invention makes it possible for a film from 0.1 nm to about 1 mm in thickness to be examined in respect of surface and refractive index structures with little required by way of apparatus.

Waveguide modes in thin transparent media are considered by P. K. Tien in Rev. Mod. Phys. 49 (1977), 361.

Waveguide modes are electromagnetic waves which can propagate in thin transparent media. The wave propagates parallel to the boundary surfaces of the medium and is damped in the propagation direction. The electromagnetic field decays exponentially to the surface of the medium.

To excite waveguide modes in thin dielectric films, especially two coupling arrangements are used: prism coupling (cf. P. K. Tien, R. Ulrich, Appl. Phys. Lett. 14 (1969), 291) and grating coupling (cf. D. G. Dalgoutte, C. D. W. Wilkinson, Appl. Optics 14 (1975), 2983).

In a prism coupler, light which has been polarized parallel or perpendicular to the plane of incidence is incident on a prism and is totally reflected at the base of the prism. The waveguide layer or layer system to be examined, which is situated on a solid support, is moved to within a few 100 nm, for example 100–400 mn, preferably 150–250 nm, of the base of the prism. If the angle of incidence of the light is right, a waveguide mode is excited in the layer or layer system to be examined. The intensity of the reflected light beam is at a minimum at that angle. The medium between the prism and the layer or layer system to be examined can be a gas or a liquid. Alternatively, the gap between the prism and the layer or layer system to be examined can be replaced by a metal or semiconductor film. The layer or layer system to be examined is then applied atop the metal or semiconductor film.

In a grating coupler, there is a solid surface with a modulation in the form of a network of lines produced by embossing or etching. This modulated surface then forms the base for the layer or layer system to be examined. As in prism coupling, the incident parallel- or perpendicular-polarized light can excite a waveguide mode in the layer or layer system to be examined if the angle of incidence is right. Again the intensity of the reflected light is at a minimum at such an angle.

Lateral structures on a layer or layer system to be determined lead to different coupling conditions for waveguide modes. If polarized light is incident upon one of the above-described sample arrangements at a fixed angle, then it is possible to detect lateral structures on the layer or layer system to be determined on the basis of differences in reflectivity or brightness. If polarized light is incident at a variable angle, the coupling conditions can be fulfilled by various areas of the layer or layer system at different angles of incidence, as a result of which lateral structures become visible.

The degree of lateral resolution is affected by the degree of damping of the waveguide mode. The degree of damping of a waveguide mode in turn is determined by the absorption and quality of the surfaces of the waveguide medium itself and by the absorption of the adjoining media. To ensure good lateral resolution, the damping of the waveguide mode should be very large.

The vertical resolution is within the subnanometer range; that is, thickness differences within a waveguide layer of less than 1 nm lead to distinctly different reflectivities and thus to observable contrasts.

The apparatus to be used according to the present invention of examining the physical properties of thin films has a simple mechanical and optical construction. It can be referred to as a waveguide mode microscope. Preferably, the waveguide modes are generated using a prism coupler constructed by adhesively bonding to the prism surface, with an immersion fluid, a microscope slide with a metal film on its back and, on top of the metal film, the layer or layer system to be examined. Alternatively, the metal film and the layer or layer system to be examined can also be in direct contact with the prism surface. The metals used for this purpose are silver, gold, copper and aluminum, and also layer systems formed from these metals. It had proven particularly advantageous to use a layer system consisting of 2-5 nm of chromium and 40 nm of gold. The resulting mirror is illuminated with parallel monochromatic colored or white parallel- or perpendicular-polarized light through one of the two free side surfaces of the prism under a flat angle and imaged through the other free side surface of the prism onto a screen, a video camera or an eyepiece with the aid of an achromatic lens of small focal length which is focused on the mirror.

Possible films for examination are thin dielectric coatings (e.g. organic polymers, silicon-containing polymers, metal oxide films) which are structured in respect of refractive index and thickness and are for example from 100 nm to 1 mm in thickness. The coatings can be applied to the metal film for example by vapor deposition, spincoating or using the Langmuir-Blodgett technique. It is also possible to examine ultrathin films from 0.1 nm to 100 nm in thickness which show refractive index and thickness structuring. To this end, the metal is advantageously first coated with a waveguide dielectric layer, for example by vapor deposition, spincoating or the Langmuir-Blodgett technique, and the dielectric medium is then coated in turn with the film to be examined, for example by the Langmuir-Blodgett (LB) technique, spincoating, absorption from the liquid phase, casting or vapor deposition. In this way it is possible to examine for example lipid monolayers, polymers, structured $SiO_2$ layers and structured cadmium arachidate LB layers.

EXAMPLE 1

The base of a prism made of SF57 glass is coated with a layer system comprising 3 nm of chromium and 40 nm of gold by vapor deposition. A structured layer of $SiO_2$ is applied on top, as the layer to be examined, by vapor deposition as follows. First 310 nm of $SiO_2$ are vapor deposited onto the metal layer system. Thereafter a further 4 nm of $SiO_2$ are vapor deposited as structuring through a mask (an electron microscopy grid).

Figure 2:
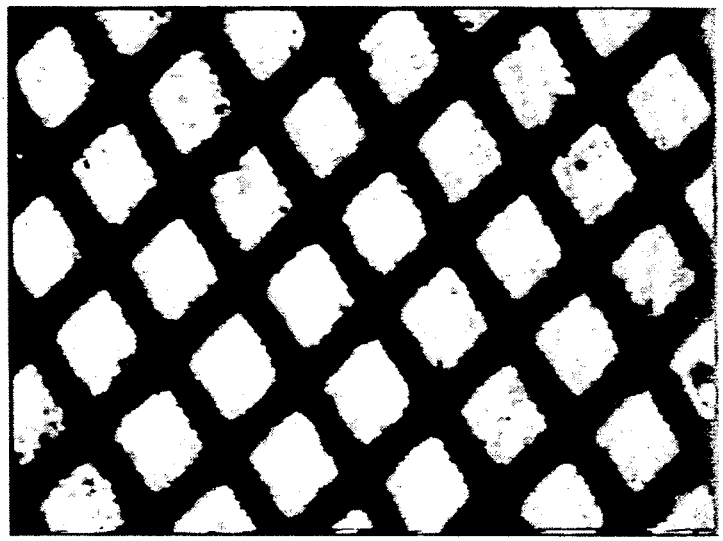
FIG. 2 shows an image of the structure $SiO_2$ made in accordance with Example 1, below.

First the reflected intensity was measured as a function of the angle of incidence of the light in homogeneous areas of the sample. The light source used was an HeNe laser ($\lambda = 633$ nm). The measurements were carried out with parallel- and perpendicular-polarized light. The waveguide modes of the 310 nm and 314 nm thick homogeneous $SiO_2$ layers occur at distinctly different angles of incidence. This shift in angle is utilized for contrast generation. FIG. 2 shows such an image of the structured $SiO_2$ layer. The black bands are 20 $\mu$m in width. The image was recorded with parallel-polarized light ($\lambda = 633$ nm) at an angle of incidence $\Theta = 31.3°$. The waveguide mode is excited in the 310 nm thick $SiO_2$ areas. The reflected intensity is minimal. For this reason these areas appear dark in the image. The 314 nm thick $SiO_2$ areas do not satisfy the coupling condition; hence no waveguide mode can be excited. These areas are bright in the image. By increasing the angle of incidence by $\Theta = 1.10°$ the contrast can be inverted, since the 314 nm thick $SiO_2$ areas then satisfy the coupling condition and excite a waveguide mode. No waveguide mode can any longer be excited in the 310 thick $SiO_2$ areas. Images recorded with perpendicular-polarized light lead to the same result.

EXAMPLE 2

The base of a prism made of SP57 glass is coated with 50 nm of silver. The silver is coated in turn by spincoating with a polyelectrolyte film (ions of the formula

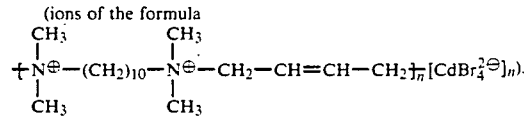

Figure 3:
FIG. 3 shows an appropriate waveguide mode micrograph of the surface of the polyelectrolyte film at $\theta = 44.5°$ in accordance with Example 2, below.

All examinations were carried out with parallel-polarized light from an HeNe laser. Measurement of the reflected intensity as a function of the angle of incidence of the light showed that only a very broad waveguide mode with low coupling can be exited in the spincoated polyelectrolyte film. A possible cause is absorption in the polyelectrolyte film, which increases the damping of the waveguide mode, or the poor surface quality of the film. The latter possibility can be checked using the method according to the present invention. FIG. 3 shows an appropriate waveguide mode micrograph of the surface of the polyelectrolyte film at $\Theta = 44.5°$. The area of the depicted detail is $570 \times 420$ $\mu m^2$. A waveguide mode can only be excited in the dark areas. The other, brighter areas differ in respect of thickness, which is why it is not possible to excite a waveguide mode at an angle of incidence of $\Theta = 44.5°$. A height line diagram can be prepared with angle-dependent images from $\Theta_1 = 43.1°$ to $\Theta_2 = 45.9°$ at $\Delta\Theta = 0.4°$. To this end, the areas of minimum grayness, i.e. the lowest reflectance, are determined in each image. These are areas of uniform thickness. By carrying out model calculations for the layer system on the basis of Fresnel's equations (cf. H. Wolter in "Handuch der Physik", S. Flügge (ed.), Springer Verlag, Berlin, 1956) it is possible to calculate the thickness corresponding to each angle. The refractive index of the material is known to be $n = 1.63$. This analysis shows that the average thickness of the layer, based on the area of size $570 \times 420$ $\mu m^2$ m investigated, is 338 nm. The thickness fluctuations area $\pm 10$ nm. This pronounced heterogeneity of the surface is responsible for the width of the waveguide mode and the poor coupling.

EXAMPLE 3

Using a lipid monolayer it will be shown how a structured ultrathin layer can be examined on top of a dielectric waveguide layer.

A microscope slide made of BK7 glass was coated with 3 nm of chromium and 40 nm of gold by vapor deposition. The metal was then coated with a 340 nm layer of $SiO_2$ by vapor deposition. This $SiO_2$ layer serves as waveguide layer.

The lipid monolayer to be examined is a Langmuir-Blodgett film of dimyristoylphosphatidic acid (DMPA). DMPA (dissolved in chloroform) is spread onto pure water and, after the solvent has evaporated, applied by the Langmuir-Blodgett technique at a pressure of 5-6 mN.m$^{-1}$ (in the coexistence phase) to the BK7 glass microscope slide prepared as described above. It is known that lipid monolayers in the coexistence phase are quasi two-dimensional systems composed of crystalline and amorphous areas. These ares should differ in respect of thickness and refractive index.

The microscope slide thus prepared is attached with an immersion fluid to a BK7 prism and examined using the method according to the present invention. The examination was carried out with parallel-polarized light from an HeNe laser. As is shown by the waveguide mode micrographs recorded at an angle of incidence of the light of $\Theta=41°$, the small thickness differences between the crystalline and amorphous areas of the DMPA are clearly resolvable not only laterally but also vertically.

The construction of the apparatus used for the technique according to the present invention is shown schematically in FIG. 1, where
1 signifies a light source,
2 the layer or layer system to be examined (e.g. a structured $SiO_2$ layer or an $SiO_2$ layer combined with a lipid monolayer),
3 the metal film,
4 a glass microscope slide,
5 the immersion fluid,
6 the glass prism,
7 a lens and
8 a video camera.

We claim:

1. In a method of thin film microscopy for examining the physical properties of thin films with the aid of polarized light, wherein the layer or layer system to be examined is irradiated with polarized light which excites waveguide modes in the layer or layer systems to be examined, and the reflected or transmitted light is deflected toward the microscopy imaging system by a coupling system comprising a prism, the improvement wherein
    the waveguide mode is dampened by the use of, as a damping layer, a separate metal or semiconductor layer associated with said prism and layer or layer system, which separate damping layer ensures good lateral resolution by damping the waveguide mode to the extent necessary to ensure good lateral translation.

2. The method of claim 1 wherein the thin film has a thickness of from 0.1 nm to about 1 nm.

3. The method of claim 2 wherein the damping layer is a metal film.

4. The method of claim 3 wherein a microscope slide is adhesively bonded to the base of the prism with an immersion fluid. the other side of the microscope slide is coated with the metal film, and the layer or layer system to be examined is situated directly on the metal film.

5. The method of claim 3 wherein the metal or semiconductor film is coated directly on the base of the prism and the layer or layer system to be examined is situated directly on the metal coated base of the prism.

* * * * *